US006896898B1

(12) United States Patent
Xiong et al.

(10) Patent No.: US 6,896,898 B1
(45) Date of Patent: May 24, 2005

(54) TRANSDERMAL DELIVERY SYSTEM FOR ALKALOIDS OF ACONITUM SPECIES

(75) Inventors: Weihong Xiong, Salt Lake City, UT (US); Dinesh C. Patel, Salt Lake City, UT (US)

(73) Assignee: XEL Herbaceuticals, Inc., Salt Lake City, UT (US)

( * ) Notice: Subject to any disclaimer, the term of this patent is extended or adjusted under 35 U.S.C. 154(b) by 876 days.

(21) Appl. No.: 09/944,960

(22) Filed: Nov. 17, 2000

Related U.S. Application Data

(60) Provisional application No. 60/166,497, filed on Nov. 19, 1999.

(51) Int. Cl.[7] ........................... A61K 9/00; A61F 13/00; A01N 43/42

(52) U.S. Cl. ........................ 424/449; 424/400; 514/279

(58) Field of Search ................................ 424/449, 400; 514/279

(56) References Cited

U.S. PATENT DOCUMENTS

| | | | | |
|---|---|---|---|---|
| 4,352,796 A | | 10/1982 | Arichi et al. | |
| 4,656,178 A | | 4/1987 | Junusov et al. | |
| 4,849,224 A | | 7/1989 | Chang et al. | |
| 4,983,395 A | | 1/1991 | Chang et al. | |
| 5,122,383 A | | 6/1992 | Heiber et al. | |
| 5,290,784 A | | 3/1994 | Qu et al. | |
| 5,446,070 A | | 8/1995 | Mantelle | |
| 5,460,820 A | | 10/1995 | Ebert et al. | |
| 5,514,684 A | | 5/1996 | Murayama et al. | |
| 5,547,956 A | | 8/1996 | Qu et al. | |
| 5,656,286 A | | 8/1997 | Miranda et al. | |
| 5,719,197 A | | 2/1998 | Kanios et al. | |
| 5,770,604 A | * | 6/1998 | Murayama | 514/279 |
| 6,024,976 A | | 2/2000 | Miranda et al. | |

FOREIGN PATENT DOCUMENTS

| | | | |
|---|---|---|---|
| CN | 1074117 A | | 7/1993 |
| JP | 1982-40144 E | * | 4/1982 |

OTHER PUBLICATIONS

Liu J–H et al. (Anti–inflammatory and Analgesic Activities of N–Deacetylappaconitine and Lappaconitine, Acta Pharmacologica Sinica, (1987), vol. 8, No. 4, pp. 301–305.*

Mamoru Ono, et al., Pharmacological Studies of Lappaconitine. Occurrence of Analgesic Effect Without Opioid Receptor, *Research Communication in Chemical Pathology and Pharmacology*, vol. 63, No. 1, Jan. 1989.

Xin Guo, et al., Lappaconitine and N–Deacetyllappaconitine Potentiate Footshock–Induced Analgesia in Rats, *Life Sciences*, vol. 48, pp 1365–1370, 1991.

Y. Bai, et al. N–Oxides of Some Norditerpenoid Alkaloids, *Journal of Natural Products*, Vo. 58, No. 6, pp. 929–933, Jun. 1995.

Guo Xin, et al., Roles of Periaqueductal Gray and Nucleus Raphe Magnus on Analgesia Induced by Lappaconitine, N–Deacetyllappaconitine and Morphine, *Acta Pharmacologica Sinica*, vol. 11, (2), pp. 107–112, Mar. 1990.

Mamoru Ono, et al., Pharmacological Studies of Lappaconitine. Analgesia Produced by Intracerebrokventricular, Intracisternal and Intrathecal Injections, *Journal of Pharmacobio–Dynamics*, 13, 374–377, 1990.

M. Ono, et al., Pharmacological Studies of Lappaconitine, *Arzneimittelforschung*, Jul. 1988; 38(7):892–5.

* cited by examiner

*Primary Examiner*—Susan Coe
*Assistant Examiner*—Randall Winston
(74) *Attorney, Agent, or Firm*—Thorpe North & Western, LLP

(57) ABSTRACT

The present invention provides a composition of transdermally administered aconitine alkaloids for ameliorating pain and inflammation. In one aspect, an aconitine alkaloid is delivered in a sufficient amount to achieve and maintain a blood plasma aconitine alkaloid level of about 0.5 ng/mL to about 400 ng/mL. Aconitine alkaloids may be delivered by themselves, or in combination with other elements, such as additional analgesics, other drugs, or positive health promoting substances. Various formulations for the transdermal delivery of aconitine alkaloids are disclosed, and may include selected penetration enhancers.

5 Claims, No Drawings

TRANSDERMAL DELIVERY SYSTEM FOR ALKALOIDS OF ACONITUM SPECIES

PRIORITY DATA

This application claims priority to provisional U.S. patent application Ser. No. 60/166,497 which was filed on Nov. 19, 1999, and which is incorporated herein by reference in its entirety.

FIELD OF THE INVENTION

The present invention relates generally to a composition and method for ameliorating pain and inflammation. More particularly, the present invention relates to a pain and inflammation ameliorating composition, which contains an alkaloid compound extracted from an *Aconitum* plant species.

BACKGROUND OF THE INVENTION

Everyone experiences physical pain in one form or another during his or her life. Pain and inflammation accompany most illnesses and physical injury. Pain may be acute or dull, intermittent, or chronic. Because of the great undesirability of pain many remedies and treatments have been sought throughout history. Further, ongoing research continues to seek analgesic and anti-inflammatory compounds that provide maximum potency with minimal adverse side effects, such as chemical dependency.

Of the various types of pain, chronic pain caused by degenerative or inflammatory diseases is considered to be especially intolerable because of its constant presence. Many diseases, such as cancer and arthritis, may cause chronic pain and inflammation, which is so debilitating that it virtually incapacitates the afflicted individual. Therefore, research efforts in the pharmaceutical and medical sciences continually seek formulations of analgesic and anti-inflammatory compounds, which are capable of long lasting high potency. The duration of potent activity is especially important when treating chronic pain in order to minimize administration frequency. By reducing administration frequency, intermittent pain, which occurs as one dosage wears off, and before another is administered, is greatly reduced.

Many analgesics such as codeine, tramadol, and dextropropoxyphene have been used to manage mild to moderate pain. Additionally, for more severe pain, opioids such as morphine, methadone, oxycodone, buprenorphine, hydromorphone, fentanyl, and heroin have been used. Unfortunately, heavy use of opioids, or other narcotics often leads to chemical dependence, or addiction.

Chemical dependence is often extremely difficult and painful to overcome. One common treatment involves administering opioids and opioid analgesics in decreasing doses over an extended duration. For example, methadone is known for treating heroin addiction by being administered in gradually decreasing amounts. While such regimens do tend to alleviate many of the withdrawal symptoms associated with detoxification, they take months to complete and are therefore only marginally successful in helping the addict take a permanent step away from chemical dependence.

SUMMARY OF THE INVENTION

It has been recognized that an analgesic agent formulation, which can be delivered with long lasting potency and at infrequent intervals would be advantageous. Additionally, it has been recognized that an analgesic agent which also imparts an anti-inflammatory effect, and which imparts minimal side effects, such as drug dependency would be advantageous.

Plant extracts from different species of *Aconitum* plant have been employed in many holistic medicine cultures for their various medicinal and positive health properties. For example, traditional Chinese medicine has long used *Aconitum* extracts for their various analgesic, anti-rheumatic, anti-narcotic, and antipyretic properties. These properties have now been largely attributed to the diterpenoid alkaloids found within the various *Aconitum* plant species.

Among the *Aconitum* plant derived alkaloids, aconitine, 3-acetylaconitine, lappaconitine, N-deacetyl-lappaconitine, songtiening, and bulleyaconitine A, have become particularly known for their powerful analgesic properties. Further, 3-acetylaconitine and lappaconitine have been shown to be centrally acting analgesics without affinity for opioid receptors.

Because extracts of Aconite roots have no affinity for opioid receptors, they may be used to expediently relieve drug addiction. In fact, lappaconitine and bulleyaconitine A dosage regimens have been shown to relieve drug dependence and remove withdrawal syndrome within 3–4 days. Significant results in such a shortened duration provide a great improvement over known treatment using successively less potent opioids.

Accordingly, in the present invention provides a transdermal formulation for ameliorating pain and inflammation. In one aspect, the transdermal formulation includes an amount of an aconitine alkaloid, which is sufficient to achieve an aconitine alkaloid blood plasma level of from about 0.5 to about 400 ng/ml, an inert carrier and, a permeation enhancer selected from the group consisting of: fatty acids, fatty acid esters, fatty alcohols, fatty acid esters of lactic acid, fatty acid esters of glycolic acid, amides, amines, pyrrolidones, glycerol triesters, terpenes, surfactants, complexing agents, biologics, their salts, and mixtures thereof. In another aspect, the blood plasma concentration of an aconitine alkaloid achieved is from about 5 to about 200 ng/ml. In another aspect, the transdermal formulation achieves the blood plasma level of from about 0.5 to about 400 ng/ml within about 0.25 to about 18 hours after administration of the formulation. In yet another aspect, the blood plasma level may be achieved within about 0.5 to about 12 hours after administration.

The transdermal formulation may be configured to provide an extended or sustained aconitine alkaloid release. In one aspect, a single dosage of the transdermal formulation may be sufficient to achieve and sustain the aconitine alkaloid blood plasma level of from about 0.5 to 400 ng/ml for a duration of at least about 24–96 hours.

Various types of aconitine alkaloids may be effective in ameliorating pain and inflammation. In one aspect, the aconitine alkaloid may be a member selected from the group consisting of lappaconitine, N-deacetyl-lappaconitine, songtiening, bulleyaconitine A, 3-acetylaconitin, isolappaconitine, deoxylappaconitine, neofinaconitine, ranaconitine, N-deacetylranaconitine, finaconitine, N-deacetylfinaconitine, mesaconitine, jesaconitine, and salts, analogs, derivatives, prodrugs, and mixtures thereof. In another aspect the aconitine alkaloid may be lappaconitine. In a further aspect, the aconitine alkaloid may be songtiening. In yet another aspect, the aconitine alkaloid may be bulleyaconitine A. In another aspect, the aconitine alkaloid may be ranaconitine. In a further aspect, the aconitine alkaloid-may be finaconitine. In another aspect, the aconitine alkaloid may be mesaconitine. In yet another aspect, the aconitine alkaloid may be jesaconitine.

In addition to an aconitine alkaloid, the transdermal delivery system of the present invention may include additional analgesics for ameliorating pain and inflammation. In one aspect, the analgesic may be a narcotic agent. In another aspect, the analgesic may be a non-narcotic agent.

In one aspect, the narcotic agent may be selected from the group consisting of: alfentanil, benzylmorphine, codeine, desomorphine, endorphins, ethylmorphine, fentanyl, hydromorphone, lavorphanol, levomethadyl acetate, meperidine, Methadone, morphine, normorphine, normethadone, opium, oxycodone, oxymorphone, remifentanil, sufentanil, tilidine, and salts, analogs, derivatives, and mixtures thereof. In another aspect, the narcotic agent may be a member selected from the group consisting of: buprenorphine, butorphanol, dezocine, eptazocine, nalbuphine, pentazocine, and salts, analogs, derivatives, and mixtures thereof.

In another aspect of the invention, the additional analgesic may be a non-narcotic agent. In one aspect, the non-narcotic agent may be a member selected from the group consisting of: acetaminophen, aspirin, clonidine, diflunisal, methotrimeprazine, salicylates, salicylic acid, tramadol, and salts, analogs, derivatives, and mixtures thereof.

In another aspect of the invention, the non-narcotic agent may be a non-steroidal anti-inflammatory drug (NSAID). In one aspect, the NSAID may be a member selected from the group consisting of: butibufen, carprofen, celecoxib, diclofenac, diflunisal, etodolac, flurbiprofen, fennoprofen calcium, flunixin meglumine, ibuprofen, idomethacitin, ketoprofen, ketorolac tromethamine, magnesium salicylate, meclofenamate sodium, mefenamic acid, naproxen, nabumetone, oxaprozin, phenylbutazone, piroxicam, rofecoxib, sulindac, tolmetin, tiaprofenic, and salts, analogs, derivatives, and mixtures thereof.

In another aspect of the invention, the non-narcotic agent may be melatonin. In a further aspect, the non-narcotic agent may be tetrahydropalmatin. In yet another aspect of the invention, the non-narcotic may be ferulic acid. In an additional aspect of the invention, the non-narcotic may be sinomenine. In yet another aspect of the invention, the non-narcotic agent may be anisodin. In a further aspect of the invention, the non-narcotic agent may be dicentrin. In another aspect of the invention, the non-narcotic agent may be anisodamin. In an additional aspect of the invention, the non-narcotic agent may be capsaicin. In a further aspect of the invention, the non-narcotic may be glucosamine. In yet another aspect of the invention, the non-narcotic may be a rhynochophylla-derived alkaloid.

The transdermal aconitine alkaloid formulation may further include one or more treatment agents, or drugs for treating specific diseases or conditions. In one aspect, the treatment agent may be an anticholinergic agent. In one aspect, the anticholinergic agent may be a member selected from the group consisting of: adiphenine, anisotropine, atropine, benzetimide, clidinium, deptropine, dicyclomine, diponium, glycopyrrolate, hydroxyzine, orphenadrine, oxybutynin, propantheline, scopolamine, as well as salts, derivatives, analogs, and mixtures thereof.

In one aspect, the treatment agent may include antimigraine agents. In one aspect, the migraine agent may be a seratonin 5-HT receptor agonist. In one aspect, the seratonin 5-HT receptor agonist may be a member selected from the group consisting of: naratriptan, rizatriptan, sumatriptin, zolmitriptan, salts, derivatives, analogs, prodrugs, and mixtures thereof. In another aspect, the anti-migraine agent may be methylsergide maleate as well as salts, derivatives, analogs, prodrugs, and mixtures thereof. In yet another aspect, the anti-migraine agent may include ergotamine derivatives. In one aspect, ergotamine derivatives may be a member selected from the group consisting of: dihydroergotamine mesylate, ergotamine tartrate, as well as salts, derivatives, analogs, prodrugs, and mixtures thereof.

In one aspect of the invention, the treatment agent may be an antiemetic/antivertigo agent. In another aspect of the invention, the antiemetic/antivertigo agent may be a member selected from the group consisting of: chloropromazine, perphenazine, prochlorperazine, promethazine, thiethylperazine, triflupromazine, metoclopramide, benzquinamide, cannabinoids, corticosteroids, hydroxyzine HCl, diphenidol, phosphorated carbohydrates, as well as salts, derivatives, analogs, prodrugs, and mixtures thereof.

The transdermal formulation of the present invention may also contain various other positive health-imparting agents. In one aspect, the health imparting agent may be a member selected from the group consisting of: vitamins, minerals, amino acids, herbal and botanical extracts, anti-oxidants, and mixtures thereof. In another aspect, the health-imparting agent may be a vitamin. In a further aspect, the health-imparting substance may be a mineral. In yet another aspect, the health-imparting agent may be an amino acid. In yet another aspect, the health-imparting agent may be an herbal extract. In another aspect of the invention, the health-imparting agent may be a botanical extract. In a further aspect of the invention, the health-imparting substance may be an anti-oxidant.

Various transdermal formulations may be used as part of the present invention for transdermally delivering aconitine alkaloids. In one aspect, the transdermal formulation may be a topical formulation. In another aspect, the transdermal formulation may be an adhesive matrix patch. In yet another aspect, the transdermal formulation may be a liquid reservoir system, or patch.

While the transdermal formulation of the present invention may include a variety of enhancers, no enhancer is necessary in order to achieve the desired blood plasma levels in many instances. Therefore, in one aspect the transdermal formulation of the present invention may be free of an enhancer.

In addition to an aconitine alkaloid transdermal formulation, the present invention encompasses a method of ameliorating pain and inflammation. In one aspect, the method includes transdermally administering an amount of an aconitine alkaloid sufficient to achieve an aconitine alkaloid blood plasma level of from about 0.5 to about 400 ng/ml. In another aspect, the transdermal administration of an aconitine alkaloid is sufficient to achieve an aconitine alkaloid blood plasma level of from about 5 to about 200 ng/ml. In a further aspect, the aconitine alkaloid blood plasma level is achieved within about 0.25 to about 18 hours after initial aconitine alkaloid administration. In yet another aspect, the aconitine alkaloid blood plasma level is achieved within about 0.5 to about 12 hours after initiation of the aconitine alkaloid administration. In a further aspect, the aconitine alkaloid blood plasma level of about 0.5 to about 400 ng/ml is sustained for a period of at least about 24–96 hours from a single transdermal administration.

The method of the present invention further encompasses the co-delivery of an aconitine alkaloid and additional pain and inflammation ameliorating substances, such as the narcotic agents and non-narcotic agents recited herein. Further, good health imparting substances, as contained herein may additionally be co-delivered with the aconitine alkaloid of the present invention.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION

Before the present formulation and method for achieving specified aconitine alkaloid blood plasma levels are disclosed and described, it is to be understood that this invention is not limited to the particular process steps and materials disclosed herein, but is extended to equivalents thereof as would be recognized by those ordinarily skilled in the relevant arts. It should also be understood that terminology employed herein is used for the purpose of describing particular embodiments only and is not intended to be limiting.

A. Definitions

In describing and claiming the present invention, the following terminology will be used.

The singular forms "a" "an," and, "the" include plural referents unless the context clearly dictates otherwise. Thus, for example, reference to "an aconitine alkaloid" includes reference to one or more of such alkaloids, reference to "an adhesive" includes reference to one or more of such adhesives, and reference to "a mineral" includes reference to a mixture of two or more of such minerals.

As used herein, the terms "aconitine alkaloid," "aconitine-derived alkaloid," or "aconitine" may be used interchangeably and refer to alkaloids, which are found in or derived from one or more species of *Aconitum* plant, including the analogues, derivatives, salts, and prodrugs, of such alkaloids, as well as mixtures thereof. Further, such alkaloids may be obtained by synthesis, extraction as a natural product from one or more *Aconitum* plant species, or by partial extracted and further synthesis.

As used herein, "analgesic" refers to a compound or agent, which imparts a pain and/or inflammatory ameliorating effect when administered.

As used herein, "narcotic," "narcotic agent," "opioid analgesic," and "opioid analgesic agent" may be used interchangeably, and refer to an analgesic, which ameliorates pain by binding to opioid receptors.

As used herein, "non-narcotic" refers to an analgesic, which ameliorates pain by a mechanism other than binding to, or otherwise occupying, opioid receptors.

As used herein, "treatment agent" or "drug" may be used interchangeably, and refer to a physiologically active substance other than aconitine or aconitine alkaloids, or other analgesic agents, which may be used to treat or improve a physiological condition. Examples of treatment agents include, but are not limited to: hormones, anticholinergics, anti-migraines, antiemetics, and mixtures thereof.

As used herein, "positive health benefit conveying, or imparting agent" and similar expressions refer to any substance either synthesized or extracted from a natural source, which is beneficial to the human body when imparted thereto. Examples of general positive health benefit conveying substances include, but are not limited to vitamins, minerals, anti-oxidants, amino acids, botanical and herbal extracts.

As used herein, "aconitine delivery formulation," "aconitine alkaloid delivery formulation," "transdermal delivery formulation," or "transdermal formulation" refer to any aconitine containing device, system, product, chemical combination, or mechanism capable of being applied to, or against the skin, to effect transdermal delivery, of aconitine alkaloids.

As used herein, the term "skin" refers to any membrane of the human body to which a chemical formulation or composition may be applied including the external skin of the body, the mucosa membranes of the nasal, oral, vaginal, and rectal cavities.

As used herein, the term "transdermal" or "percutaneous" delivery means delivery of a substance or agent, by passage into and through the skin. Hence the terms "transdermal" and "transmucosal" are used interchangeably unless specifically stated otherwise. Likewise, the terms "skin", "derma", "epidermis", "mucosa", and the like shall also be used interchangeably unless specifically stated otherwise.

As used herein, the terms "enhancement", "penetration enhancement", or "permeation enhancement" refer to an increase in the permeability of the skin, to a delivery substance or agent, so as to increase the rate at which the delivery substance permeates through the skin. "Permeation enhancer", "enhancer", "penetration enhancer", or similar terms refer to a material, or materials that achieve or facilitate such permeation enhancement, and an "effective amount" of an enhancer means an amount effective to enhance penetration through the skin, of an aconitine alkaloid, to a selected degree. An index of permeation enhancers is disclosed by David W. Osborne and Jill J. Henke, in their publication entitled *Skin Penetration Enhancers Cited in the Technical Literature*, published in "Pharmaceutical Technology" (June 1998), which may also be found at the worldwide web address known as: pharmtech.com/technical/osborne/osborne.htm, which is incorporated by reference herein. Enhanced permeation as affected through the use of such enhancers can be observed, for example, by measuring the rate of diffusion of the delivery substance through animal or human skin using a diffusion cell apparatus. Such a diffusion cell is described by Merritt et al., Diffusion Apparatus for Skin Penetration, J. of Controlled Released 61 (1984), incorporated herein by reference.

As used herein, "effective amount" refers to the minimal amount of a substance or agent, which is sufficient to achieve a desire therapeutic effect. Therefore, when used in connection with an aconitine alkaloid, effective amount connotates an amount of such agent, which is sufficient to achieve a desired aconitine alkaloid plasma level. Such plasma levels may be achieved within and sustained for various time intervals as determined by the parameters of each particular formulation. The type and amount of aconitine alkaloid, the type and amount of inert carrier, the size of the transdermal formulation, as well as the presence and amount of specific penetration enhancers may all be adjusted to arrive at a formulation which achieves the desired blood levels within a specific time interval. One of ordinary skill in the transdermal arts would be able to readily determine the amount and type of each component in the combination, which are required to achieve the target blood levels within a specified time frame.

By the term "matrix", "matrix system", or "matrix patch" is meant a pre-determined amount of an aconitine alkaloid dissolved or suspended in a polymeric carrier or phase, in one aspect a pressure-sensitive adhesive, that can also contain other ingredients, or in which a permeation enhancer and other positive health benefit promoting substances may also dissolved or suspended. This definition is meant to include embodiments wherein such polymeric phase is laminated to a pressure sensitive adhesive or used within an overlay adhesive to form an adhesive matrix patch with a reservoir. A matrix system usually and preferably comprises an adhesive layer having an impermeable film backing laminated onto the distal surface thereof and, before transdermal application, a release liner on the proximal surface of the adhesive. The film backing protects the polymeric phase of the matrix patch and prevents release of the delivery substance and/or enhancer to the environment. The release liner function similarly to the impermeable backing, but is removed from the matrix patch prior to application of the patch to the skin as defined above. Matrix patches are known in the art of transdermal delivery to routinely contain such backing and release liner components, and matrix patches according to the present invention should be considered to comprise such backing and release liner or their functional equivalents. A matrix system therefore is a unit dosage form, or type of formulation, which includes a predetermined amount of an aconitum alkaloid, as well as other optional ingredients, such as additional analgesics, and good health-imparting ingredients, in a polymeric carrier, which optionally contains an enhancer. Examples without limitation, of adhesive matrix transdermal patches are those described or referred to in U.S. Pat. Nos. 5,122,383 and 5,460,820, which are incorporated by reference in their entirety.

As used herein, "liquid reservoir system," its acronym "LRS," or "liquid reservoir patch" refers to a transdermal delivery patch or system, in which an aconitine alkaloid and other optional ingredients, such as a permeation enhancer, are admixed with a carrier vehicle. The carrier vehicle comprises a fluid of desired viscosity, such as a gel or ointment, which is formulated for confinement in a reservoir having an impermeable backing and a skin contacting permeable membrane, or membrane adhesive laminate providing diffusional contact between the reservoir contents and the skin. For application, a peelable release liner is removed and the patch is attached to the skin surface. LRS patches are known in the art of transdermal drug delivery. Examples without limitation, of LRS transdermal patches are those described or referred to in U.S. Pat. Nos. 4,849,224, 4,983,395, which are incorporated by reference in their entirety.

As used herein, "inert carrier" refers to a polymeric carrier, or other carrier vehicle into which aconitine, or an aconitine-derived alkaloid may be admixed in order to form a transdermal delivery formulation. Inert carriers must generally be pharmaceutically acceptable, in that they are suitable for administration to the skin without causing significant instances of adverse results. Further, inert carriers must not react with the active substance to substantially degrade it, or otherwise form impurities, which may be delivered to the skin.

As used herein, "topical formulation" refers to a chemical formulation in which an aconitine alkaloid may be incorporated, which is capable of being applied directly to the skin, and which does not include supporting structures such as backing films, etc. Examples of topical formulations without limitation include, gels, aerosols, creams, lotions, pastes, ointments, etc.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 ng/ml should be interpreted to include not only the explicitly recited concentration limits of 0.5 ng/ml and 400 ng/ml, but also to include individual concentrations within that range, such as 0.5 ng/ml, 0.7 ng/ml, 1.0 ng/ml, 5.2 ng/ml, 8.4 ng/ml, 11.6 ng/ml, 14.2 ng/ml, 100 ng/ml, 200 ng/ml, 300, ng/ml, and sub-ranges such as 0.5–2.5 ng/ml, 4.8–7.2 ng/ml, 6–14.9 ng/ml, 55 ng/ml, 85 ng/ml, 100–200 ng/ml, 117, ng/ml, 175 ng/ml, 200–300 ng/ml, 225 ng/ml, 250 ng/ml, and 300–400 ng/ml, etc. This interpretation should apply regardless of the breadth of the range or the characteristic being described.

B. The Invention

The present invention encompasses a transdermally administered aconitine alkaloid formulation for ameliorating pain and/or inflammation. In one aspect, the aconitine alkaloid is administered in an amount sufficient to affect and maintain an aconitine alkaloid blood plasma level of about 0.5 ng/mL to about 400 ng/mL. In another aspect, the blood plasma level may be about 5 ng/mL to about 200 ng/mL.

The time frame for achieving such blood plasma levels may be determined by such parameters as the type and size of the aconitine alkaloid formulation, the amount of alkaloid present in the formulation, and the skin flux rate achieved by the formulation. Further, the flux rate may be determined in part by the presence and amount of various penetration enhancers.

Elements such as patch size, aconitine alkaloid content and concentration, enhancer amount, and enhancer type may all be coordinated in order to achieve the desired blood plasma levels within a desired amount of time, as can be readily determined by one skilled in the art. Others physiological factors, such as variations in individual skin type and permeability may effect the ultimate aconitine alkaloid blood plasma level and the time frame in which it is achieved.

The aconitine blood plasma levels, which will result from a particular aconitine alkaloid formulation determined using the following First Order Elimination and Zero-Order Input equations in connection with single compartment skin flux data.

$$Cp = \frac{k_0}{V_d K_{el}}\left\{1 - e^{-K_{el}{}^1}\right\} \quad \text{During input period } (t \geq T)$$

$$Cp = \frac{k_0}{V_d K_{el}}\left\{1 - e^{-K_{el}{}^1}\right\}e^{-K_{el}(1-T)} \quad \text{After input period } (t < T)$$

$Cp$: Plasma concentration (ng/ml or µg/ml)

$k_0$: Zeor-order input rate (µg/$h$, interval skin flux)

$Cl$: Clearance = $V_d * K_{el}$(L/hr/kg)

$Vd$: Volume of distribution (L or L/kg)

$Kel$: First-order elimination rate constant $T$: Duration of zero-order input $t$: $t$ time point of plasma concentration As a result, the coordination of the various above-recited aconitine alkaloid transdermal formulation parameters in order to achieve and sustain a desired aconitine alkaloid blood plasma level may readily be determined by one skilled in the art.

In one aspect, permeation rates of aconitine alkaloids through living human skin may be in the range of about 0.1 ug/cm$^2$/hr to about 50 ug/cm$^2$/hr. In another aspect, therapeutic blood levels may be achieved in about 0.25–18 hours after initial formulation application. In a further aspect, therapeutic blood levels may be achieved in about 0.5 to about 12 hours after initial formulation application. In yet another aspect, the aconitine alkaloid dosage arriving from a limited area of skin may be from about 0.1–20 mg over a period of 24 hours. In yet another aspect, the aconitine alkaloid dosage arriving from a limited area of skin may be from about 1–10 mg over a 24-hour period. In one aspect, the dosage for lappaconitine may be from about 4–10 mg over a period of about 24 hours. In an additional aspect, the dosage for 3-acetylaconitine may be from about 0.2–1 mg over a 24-hour period. In yet another aspect the dosage for bulleyaconitine A may be from about 0.2–2 mg over a 24-hour period. In a further aspect, the transdermal formulation may have a size of from about 1–200 cm$^2$. In another aspect, the size of the transdermal formulation may be from about 5–100 cm$^2$.

However, these general parameters are not limitations on the way in which the desired blood serum levels may be achieved. Different permeations, times, and amounts may be used to effect the desired blood levels by employing a formulation which uses different parameters.

By adjusting parameters such as the size and type of the transdermal formulation, the speed and duration of aconitine alkaloid delivery may be varied. In one aspect of the present invention, a single dosage of the transdermal delivery formulation may achieve and sustain the aconitine alkaloid plasma level of from about 0.5 to about 400 ng/ml for a duration of at least about 24–96 hours.

Specific aconitine alkaloid delivery formulation types include but are not limited to: 1) topical formulations such as ointments, lotions, gels, pastes, mousses, aerosols, and skin creams; 2) transdermal patches such as adhesive matrix patches and liquid reservoir systems; 3) transmucosal tablets such as buccal or sublingual tablets or lozenges; and 4) suppositories. In short, any transdermal administration form is acceptable.

In one aspect, the aconitine alkaloid delivery formulation may also include a permeation enhancer, or mixture of permeation enhancers in order to increase the permeability of the skin to aconitine alkaloids. A wide range of known permeation enhancers have been found to enhance the delivery of aconitine alkaloids and include but are not limited to: fatty acids, fatty acid esters, fatty alcohols, fatty acid esters of lactic acid or glycolic acid and their salts, amides, amines, pyrrolidones, glycerol triesters, terpenes, classical surfactants, organic acids, surfactants, complexing agents, biologics, and mixtures thereof.

One enhancer that has been found to be unacceptable is Azone. Although Azone may provide penetration enhancement of various substances, the side effects experienced are considered intolerable. Particularly, Azone has been deemed unusable because of the severe skin irritation that results. Not only does Azone cause irritation to all layers of the epidermis, but also irritates all the dermis layers as well. Further, the skin irritation caused by Azone is irreversible damage, which results in alteration of the tissue and scarring.

Specific examples of acceptable fatty acids include but are not limited to, oleic acid, alkanoic acids, capric acid, hexanoic acid, lactic acid, lauric acid, linoleic acid and mixtures thereof.

Specific examples of acceptable fatty acid esters include but are not limited to methyl laurate, glycerol monooleate (GMO), sorbitan monooleate (SMO), glycerol monolaurate (GML), glycerol monolinoleate (GMLO), isopropyl myristate, isopropyl palmitate, methyl propionate, monoglycerides, propylene glycol monolaurate, sorbitan monolaurate, and mixtures thereof.

Specific examples of acceptable fatty alcohols include but are not limited to lauryl alcohol, caprylic alcohol, myristyl alcohol, cetyl alcohol, aliphatic alcohols, linolenyl alcohol, nerolidol, oleyl alcohol, and mixtures thereof.

Specific examples of acceptable fatty acid esters of lactic acid or glycolic acid or their salts include but are not limited to lauroyl glycolate, sodium lauryol glycolate, caproyl glycolate, sodium caproyl glycolate, cocyl glycolate, sodium cocyl glycolate, isostearoyl glycolate, tromethamine lauroyl glycolate, lauroyl lactylate, sodium lauroyl lactylate, caproyl lactylate, sodium caproyl lactylate, cocoyl lactylate, sodium cocyl lactylate, isostearoyl lactylate, tromethamine lauryol lactylate, and mixtures thereof.

Specific examples of acceptable amides include but are not limited to lauramide diethanolamide, alkanolamides, ethoxylated alkanolamides, ethylene bisamides, urea, and mixtures thereof.

Specific examples of acceptable pyrrolidones include but are not limited to N-methyl-pyrrolidone N-alkyl-pyrrolidones, pyrrolidone carboxylic acids, pyrrolidone catboxylic esters, and mixtures thereof.

Specific examples of acceptable glycerol triesters include but are not limited to triacetin, diacetin, monoacetin, tributylrin, tricaproin, tricaprylin, trilaurin, trymyristin, tripalmitin, tristearin, triethyl citrate, tributyl citrate, and mixtures thereof.

Specific examples of acceptable terpenes include but are not limited to lemonene, methone, pipertone, 1-8 cineole, terpineol, terpinen-4-ol pulegone, carvone, carveol, and mixtures thereof.

Specific examples of acceptable amines include but are not limited to lauryl-amine (dodecylamine), unsaturated cyclic ureas, urea, and mixtures thereof.

Specific examples of acceptable classical surfactants include, but are not limited to Brij surfactants, (such as Brij 30, Brij 36T, Brij, 35, Brij 52), Pluronic surfactants, (such as Pluronic F68, and Pluronic L62), Span surfactants, (such as Span 20 and Span 85), Tween surfactants, (Such as Tween 20, Tween 40, and Tween 80), Poloxomer surfactants, Myrj surfactants, bile salts, sodium laurate, sodium lauryl sulfate, and mixtures thereof.

Specific examples of acceptable complexing agents include but are not limited to cyclodextrine complexes and derivatives thereof, liposomes, microcapsules, microspheres, and mixtures thereof.

Specific examples of organic acids include, but are not limited to salicylic acid, citric acid, salicylates, and mixtures thereof.

Specific examples of acceptable biologics include but are not limited to L-α-amino acids, lecithin, phospholipids, and mixtures thereof.

In addition to those enhancer substances enumerated above, many natural substances are capable of acting as permeation enhancers. These natural substances include, but are not limited to: arecoline, berbamine, berberine, camphol, capsaicin, capsaicine, capsic acid, eucalyptus (oil), eucalyptols, ferulic acid, menthol, oleummenthae, paeonol, peppermint oil, tanshinone, and mixtures thereof.

The aconitine alkaloids used in the formulation of the present invention may be those found in many species of *Aconitum* plant. Examples of various *Aconitum* species include, but are not limited to: *Aconitum sinomoritanum*

Nakai, *A. finetianum* Hand-Mazz., *A. episcopale* Le'vl, *A. bulleyanum* Diels, *A. coreanum* (Levl.) Raipaics, *A. tatsinenense, A. pendulum, A. japonicum* Thunberg, *A. sinense* Siebold, *A. zuccarini* Nakai, *A. Subcuneatum* Nakai, *A. aizuense* Nakai, *A. sanyoense* Nakai, *A. napellus* Linne, *A. carmichaeli* Debeaux, *A. volubile* Pallas, *A. chinense* Paxton, *A. Fischeri* Reichenbach, *A. yesonense* Nakai, *A. Sachalinense* Fr. ScHM, *A. Koreanum* R. Raymond, *A. ferox* Wall, *A. deinorrhizum* Stapf, *A. teterophyllum* Wall, *A. palmatum* Raymond, *A. lozyanum* R. Raymond, *A. pterocaule* Koidz, *A. gigas* LEV. el VAN, *A. senanense* Nakai, *A. matsumurae* Nakai, *A. metajapanicum* Nakai, *A. nakusanense* Nakai, *A. yuparense* Takeda, *A. kusnezoffic* Reichenbach, *A. manshuricum* Nakai, *A. vilmorinianum* Kom., *A. paniculigerum* Nakai, *A. artemisaefolium* Bar.et Skv., *A. taipeicum* Hand-Mazz., *A. stylosum* Staph, *A. karakolicum* Rap., *A. soongarium* Stapf, *A. hemsleyanum* Pritz., *A. delavayi* Franch., *A. sungpanense* Hand.-Mazz., *A. balfourii* Stapf, *A. richardsonianum* Lauener, and *A. transsectum* Diels.

Whether synthesized, extracted, or produced by a combination of such processes, a wide variety of aconitine alkaloids may be used in the transdermal formulation of the present invention. General alkaloid types may be aconines, aconitines, aconitanes, and mixtures thereof. Specific examples of aconitine alkaloid species include without limitation, lappaconitine, N-deacetyl-lappaconitine, songtiening, bulleyaconitine A, 3-acetylaconitin, isolappaconitine, deoxylappaconitine, neofinaconitine, ranaconine, ranaconitine, N-deacetylranaconitine, finaconitine, N-deacetylfinaconitine, mesaconitine, jesaconitine, and salts, analogs, derivatives, prodrugs, and mixtures thereof. Other aconitine alkaloids considered to be within the scope of the present invention are disclosed in U.S. Pat. Nos. 5,290,784, 5,547,956, 5,514,684, and 5,770,604, which are incorporated herein by reference in their entirety.

In addition to an *Aconitum* alkaloid, the transdermal delivery system of the present invention may include additional analgesics for ameliorating pain and inflammation. Such analgesics may be either narcotic or non-narcotic.

Specific examples of acceptable narcotic agents include, but are not limited to, alfentanil, benzylmorphine, codeine, desomorphine, endorphins, ethylmorphine, fentanyl, hydromorphone, lavorphanol, levomethadyl acetate, meperidine, Methadone, morphine, normorphine, normethadone, opium, oxycodone, oxymorphone, remifentanil, sufentanil, tilidine, buprenorphine, butorphanol, dexocine, eptazocine, nalbuphine, pentazocine, and salts, analogs, derivatives, and mixtures thereof.

Other analgesics for inclusion with the transdermal formulation of the present invention may be non-narcotic agents. Examples of acceptable non-narcotic agents include without limitation, acetaminophen, aspirin, clonidine, diflunisal, methotrimeprazine, salicylates, salicylic acid, tramadol, and salts, analogs, derivatives, and mixtures thereof. Further examples of acceptable non-narcotic agents include without limitation, NSAID's, such as butibuferi, carprofen, celecoxib, diclofenac, diflunisal, etodolac, flurbiprofen, fennoprofen calcium, flunixin meglumine, ibuprofen, idomethacetin, ketoprofen, ketorolac tromethamine, magnesium salicylate, meclofenamate sodium, mefenamic acid, naproxen, nabumetone, oxaprozin, phenylbutazone, piroxicam, rofecoxib, sulindac, tolmetin, tiaprofenic, and salts, analogs, derivatives, and mixtures thereof.

Specific examples of other non-narcotic agents that are suitable for inclusion in the transdermal formulation of the present invention include without limitation, melatonin, tetrahydropalmatin, ferulic acid, sinomenine, anisodin, dicentrin, anisodamin, capsaicin, glucosamine, rhynochophylla-derived alkaloids.

The aconitine alkaloid formulation of the present invention may further include other treatment agents for treating a condition or disorder with which pain is associated. Examples of such treatment agents include without limitation, anticholinergic agents, such as, adiphenine, anisotropine, atropine, benzetimide, clidinium, deptropine, dicyclomine, diponium, glycopyrrolate, hydroxyzine, orphenadrine, oxybutynin, propantheline, scopolamine, as well as salts, derivatives, analogs, prodrugs, and mixtures thereof.

Other treatment agents may include anti-migraine agents such as seratonin 5-HT receptor agonists, including, but not limited to members selected from the group consisting of: naratriptan, rizatriptan, sumatriptin, zolmitriptan, salts, derivatives, analogs, prodrugs, and mixtures thereof. Other anti-migraines include, methylsergide maleate and ergotamine derivatives, such as dihydroergotamine mesylate, ergotamine tartrate, as well as salts, derivatives, analogs, prodrugs, and mixtures thereof.

Additional treatment agents, which may be included in the aconitine alkaloid composition of the present invention, are antiemetic/antivertigo agents. Examples of specifically acceptable antiemetics/antivertigo agents include without limitation, chloropromazine, perphenazine, prochlorperazine, promethazine, thiethylperazine, triflupromazine, metoclopramide, benzquinamide, cannabinoids, corticosteroids, hydroxyzine HCl, diphenidol, phosphorated carbohydrates, as well as salts, derivatives, analogs, prodrugs, and mixtures thereof.

The transdermal formulation of the present invention may also contain various other positive health-imparting agents. and salts, derivatives, analogs, and mixtures thereof.

Other analgesic substances not specifically mentioned may be used in connection with the present invention. Such analgesics include both narcotic and non-narcotic agents. Such analgesic substances, as well as other drugs and treatment agents that may be included in the aconitine alkaloid formulation of the present invention may be found in U.S. Pat. Nos. 5,446,070, and 5,719,197, which are incorporated herein by reference in their entirety. Additional analgesic substances, as other drugs and treatment agents that may be included in the aconitine alkaloid formulation of the present invention may be found in the publication "Drug Facts and Comparisons" (January 2000), which is incorporated herein by reference.

Further, aconitine alkaloids may be combined with other positive health benefit conferring substances, or treatment agents, either before, during, or after its inclusion in the transdermal delivery formulation. Such positive health benefit conferring substances include but are not limited to vitamins, amino acids, minerals, herbal and botanical extracts, anti-oxidants, other materials which are essential to the body, and mixtures thereof.

Specific examples of acceptable vitamins include both water-soluble and oil soluble vitamins. Water-soluble vitamins include but are not limited to the B1, B2, B3, B4, B5, B6, B12, B13, B15, B17, biotin, choline, folic acid, inositol, para-amino benzoic acid (PABA), Vitamin C, Vitamin P, and mixtures thereof. Additionally, oil soluble vitamins include Vitamin A, Vitamin D, Vitamin E, Vitamin K and mixtures thereof.

Specific examples of acceptable amino acids include but are not limited to alanine arginine, carnitine, gammaaminobutyric acid (GABA), glutamine, glycine, histidine, lysine, methionine, N-acetyl systeine, ornithine, phenylalanine, taurine, tyrosine, valine, and mixtures thereof.

Specific examples of acceptable minerals include but are not limited to calcium, potassium, iron, chromium, phosphorous, magnesium, zinc, copper and mixtures thereof, as well as any other minerals essential to the human body.

Specific examples of acceptable herbs and botanical extracts include but are not limited to Asarum L. sieboldi Mig., Camphol, Clove (Flos syzygii Aromatici), *Corydalis ambigua*, Danshen (salvia miltiorrhize), Dongui (Radix angelicae sinensis), Forsythia suspensa (thunb.) Vahl., Ginseng, *Ginkgo Biloba, Impatients balsamina* L. Ib., *Ligusticum wallichii* Franch, Myrrha, Olibanum, Pearl, Polygalaceae L., *Speranskia tuberculata* Bail, St., St. John's Wort, Valerian, and mixtures thereof.

Specific examples of acceptable antioxidants include but are not limited to polyphenols such as catechin, beta-carotene, coenzyme Q10, grapnel, and mixtures thereof.

The aconitine alkaloids, analgesics, and other positive health benefit conveying substances, may be either produced synthetically, or harvested from plants and other natural sources by methods such as extraction and concentration. In short, the source of the delivery substance may be either artificial, natural, or a combination thereof.

In one aspect, the transdermal delivery formulation of the present invention may be a topical formulation. As recited above, topical formulations may take a variety of specific forms, such as gels, ointments, pastes, aerosols, creams, lotions, and other hydrophobic or water-miscible vehicles. Other specific types of topical formulations not specifically mentioned will be readily recognized by those skilled in the art and fall within the purview of the present invention.

Specific examples of suitable hydrophobic and water-miscible agents include but are not limited, hydrocarbons (e.g. liquid paraffin, mineral oil, paraffin oil, white petrolatum, squalane), silicones (e.g. liquid polymethylsilaxanes, dimethicone), alcohols (e.g. ethanol, isopropyl alcohol, lauryl alcohol), polyols and polyglycols (e.g. propyl glycol, glycerin, triacetin, polyethylene glycols), Sterols (e.g. lanolin, cholesterol), carboxylic acids (e.g. lauric acid, oleic acid), esters and polyesters (e.g. ethylene glycol monostearate, sorbitan monoesters, glyceryl tristearate, olive oil, soybean oil, isopropyl myristate, isopropyl palmitate).

Specific examples of suitable emulsifiers include, but are not limited to sterols and sterol eaters (e.g. cholesterol), carboxylic acid salts (sodium, ethanol amine, etc. of lauric acid, oleic acid, etc.), esters and polyesters (e.g. ethylene glycol monoesters, propylene glycol monoesters, glycerol monoesters, sorbitan monoesters, sorbitol monoesters, polyoxyethylene esters, sorbitan diesters, polyoxy ethylene sorbitan polyesters-tweens), ethers and polyethers (e.g. polyethylene glycol monocetyl ethers, polyethylene-polypropylene glycols-pluronics), others (e.g. sodium lauryl sulfate, borax, ethanolamine).

Specific examples of suitable thickeners include, but are not limited to acrylate copolymers, algin, behenyl alcohol, 18–36 acid triglycerides, calcium carboxymethyl celluse, PVP/MA copolymers, carbomer (910, 934, 934p, 940, 941, 1342), carboxymethylcelluse sodium, cellulose, cetyl alcohol, guar gum, hydroxyethylcellulose, hydroxypropylcellulose, hydroxypropylmethylcellulose, methylcellulose, methyl hydroxyethylcellulose, PEGs, poloxamine (304, 504, 701, 904, 1102, 1304, 1502, etc.), polycarbophil, polyethylene, propylene glycol alginate, PVP, PVP/VA copolymer, silica, silicones, beeswax.

The transdermal delivery formulation of the present invention may take the form of an occlusive device, such as a transdermal patch, in order to provide an aconitine alkaloid formulation. Such a transdermal patch may either be an adhesive matrix patch, a liquid reservoir system type patch, a buccal or sublingual tablet, lozenge, or the like.

In the case of the adhesive matrix patch, an amount of an aconitine alkaloid sufficient to produce the desired therapeutic blood plasma level is dissolved or suspended in a polymeric phase or carrier. A selected permeation enhancer, or mixture of enhancers may be included in the polymeric phase, as well as additional positive health benefit imparting substances as mentioned above. The size of an adhesive matrix patch may be adjusted to provide varying dosage amounts, and may vary from about 1 to 200 $cm^2$. In another aspect, the size of an adhesive matrix patch may be from about 5 to about 100 $cm^2$.

A wide range of adhesives useful in connection with transdermal patches will be known to those skilled in the art of transdermal drug delivery. In one aspect of the invention, acceptable adhesives may include polyacrylate polymers, rubber-based adhesives, and polysiloxanes adhesives.

In one aspect, polyacrylate polymers can be any of the homopolymers, copolymers, terpolymers, and the like of various acrylic acids. In another aspect of the invention, the acrylate polymers may be a combination of one or more monomers of acrylic acids and other copolymerizable monomers.

Acrylate polymers may also include copolymers of alkyl acrylates and/or methacrylates, and/or copolymerizable secondary monomers or monomers with functional groups. Specific examples of acrylate monomers, which are suitable for use with the present invention include, but are not limited to methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecylmethacrylate, tridecyl acrylate, tridecyl methacrylate, and mixtures thereof.

Specific examples of functional monomers which are copolymerizable with the above-recited alkyl acrylates or methacrylates, which can also be used include, but are not limited to acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxethyl acrylate, methoxyethyl methacrylate, and mixtures thereof.

Further details and examples of acrylic adhesives which are suitable for use in the present invention are set forth in Satas, *"The Handbook of Pressure-sensitive Adhesive Technology,"* $2^{nd}$ ed,. Pp. 396–456 (1989), which is incorporated herein by reference in its entirety.

Examples of suitable acrylic adhesives which are commercially available include polyacrylate adhesives sold under the trademarks DUROTAK® by National Starch and Chemical Corporation, Bridgewater, N.J., as well as GELVA-MULTIPOLYMER SOLUTION® Monsanto, St. Louis, Mo. Other examples of adhesives, and adhesive formulations, which can be used in connection with the present invention are disclosed in U.S. Pat. No. 5,656,286, which is incorporated herein by reference in its entirety.

In one aspect, utilizing a mixture of two or more acrylic polymers may facilitate sustained release of aconitine alkaloids. Many variations and combinations of acrylics may be employed to achieve the desired increase in release duration. Examples of such combinations may be found in U.S. Pat. No. 6,024,976, which is incorporated herein by reference in its entirety. Other examples of such acrylic combinations will be readily recognized by those skilled in the art.

Specific examples of suitable rubber-based pressure sensitive adhesives include, but are not limited to hydrocarbon polymers, such as natural and synthetic polyisoprenes, polybutylenes and polyisobutylene (PIB), styrene/butadiene polymers, styrene-isoprene-styrene block copolymers, hydrocarbon polymers such as butyl rubber, halogen-containing polymers such as polyacrylic nitrile, polytetrafluoroethylene, polyvinyl chloride, polyvinylidene chloride, and polychlorodiene, and polysiloxanes, and other copolymers thereof.

Specific examples of suitable polysiloxanes include but are not limited to silicone pressure sensitive adhesives, which are a based on two major components: a polymer, or gum, and a tackifying resin. The polysiloxane adhesive may be prepared by cross-linking the gum, typically a high molecular weight polydiorganosiloxane with the resin to produce a three-dimensional silicate structure via a condensation reaction in an appropriate organic solvent. Various aspects of formulating polysiloxane adhesives are disclosed by Sobieski et al, in "Silicone Pressure sensitive Adhesives," I.d. at Pp. 508–517, which is incorporated herein by reference.

Suitable silicone pressure-sensitive adhesives are commercially available and include the silicone adhesives sold under the trademarks BIO-PSA® Dow Corning Corporation, Medical Products, Midland, Mich.

In use, the matrix patch contains a distal backing and a proximal release liner laminated on the polymer layer. The distal backing defines the side of the matrix patch that faces the environment, (i.e., distal to the skin or mucosa), and the release liner is adhered to the proximal side and must be removed before patch application. The backing layer functions to protect the matrix polymer layer with the delivery substances and optional enhancer, and to provide an impenetrable layer that prevents loss of delivery substance to the environment. Thus, the material chosen for the backing should be compatible with the polymer layer, delivery substances, and enhancer, and should be minimally permeable to any components of the matrix patch.

Advantageously, the backing can be opaque to protect components of the matrix patch from degradation caused by exposure to ultraviolet light. Further, the backing should be capable of binding to and supporting the polymer layer, yet should be pliable to accommodate the movements of a person using the matrix patch.

Suitable materials for the backing include, but are not limited to: metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene. A thickness of about 0.0005 to about 0.01 inch may be preferred. The release liner can be made of the same materials as the backing, or other suitable films coated with an appropriate release surface.

The matrix patch can further comprise various additives in addition to the polymer layer, delivery substances, and permeation enhancer that are the fundamental components of the adhesive matrix patch formulation. These additives are generally those pharmaceutically acceptable ingredients that are known in the art of transdermal substance delivery and, more particularly, in the art of transdermal substance delivery. However, such additive ingredients must not materially alter the basic and novel characteristics of the matrix patch. For example, suitable diluents can include mineral oil, low molecular weight polymers, plasticizers, and the like. Many transdermal delivery substance formulations have a tendency to irritate the skin after prolonged exposure thereto, thus addition of a skin irritation reducing agent aids may be desirable.

The LRS patch generally contains a backing layer having a reservoir portion configured to contain the carrier vehicle in which the aconitine alkaloid is admixed or dissolved. Such carrier vehicles may be the same as those used for topical applications described above. Further, a micro porous membrane may be heat sealed across the opening of the reservoir in order to control the rate at which the aconitine alkaloid is transmitted to the skin. Additionally, an adhesive layer will generally be applied to a portion of the backing layer surrounding the reservoir for adhering the LRS patch to the skin. Further, a release liner that is removed prior to application is placed upon the adhesive to prevent adhesion of the patch prior to application.

In use, the release liner is removed, and the patch is adhered to the skin at a selected application situs. When the contents of the reservoir have been depleted, the patch may be removed.

C. Examples and Experimentals

The following examples of transdermal formulations having a variety of aconitine alkaloid containing formulations are provided to promote a more clear understanding of the possible combinations of the present invention, and are in no way meant as a limitation thereon.

In vitro human cadaver skin flux studies were conducted using modified Franz non-jacketed permeation cells. The temperature of the skin surface was maintained at 32° C. by placing the cells in a circulating water bath positioned over a stirring module. The epidermal membrane was separated from the human cadaver whole skin by the heat-separation method of Kligman and Christopher (*Arch. Dermatol.* 88:702 (1963)) involving the exposure of the full thickness skin to 60° C. heat for 60 seconds, after which time the stratum corneum and the epidermis (epidermal membrane) were gently peeled off the dermis.

For matrix skin flux study, the heat separated human epidermal membrane was cut into rectangular strips. The matrix was cut into 0.71 $cm^2$ circular discs. The release liner was peeled and discarded and the matrix disc was laminated onto the stratum corneum surface of the epidermal membrane. The skin-matrix sandwich was then loaded onto the diffusion cells. Each piece of the skin matrix sandwich was loaded between the donor and receiver compartments of a diffusion cell, with the epidermal side facing the receiver compartment, and clamped in place. The receiver compartment was then filled with 0.02% sodium azide aqueous solution. The solubility of the drug in this medium is adequate to ensure sink conditions throughout the experiment. The diffusion cell was then placed in a circulating water bath calibrated to maintain the skin surface temperature at 32±1° C. At predetermined sampling intervals, the entire contents of the receiver compartment were collected for drug quantitation and the receiver compartment was filled with fresh receiver solution, taking care to eliminate any air bubbles at the skin/solution interface.

For gel skin flux study, the epidermal membrane was cut and placed between two halves of the permeation cell with the stratum corneum facing the donor compartment. The skin was allowed to hydrate at 32° C. overnight with 0.02% (w/v) sodium azide solution in the receiver compartment. The following morning, 75 µl of a gelled formulation was placed into a cavity created by placing a Teflon washer over the stratum corneum surface. The cavity was then occluded by clamping an occlusive backing over the Teflon washer and gel. A 0.02% sodium azide aqueous solution was placed in the receiver compartment in contact with the dermal side of the epidermis, to ensure sink conditions for the drug. At predetermined sampling intervals, the entire contents of the receiver compartment were collected for drug quantitation and the receiver compartment was filled with fresh receiver solution, taking care to eliminate any air bubbles at the skin/solution interface.

The cumulative amount of drug permeated per unit area at any time t ($Q_t$, ug/cm$^2$) was determined as follows:

$$Q_t = \sum_{n=0}^{t} (C_n * V)/A$$

where $C_n$ is the concentration (µg/ml) of the drug in the receiver sample for the corresponding sample time, V is the volume of fluid in the receiver chamber (~6.3 cm$^3$), and A is the diffusion area of the cell (0.64 cm$^2$). The slope of the best fit line to the $Q_t$ vs. t plot gives the steady state flux ($J_{ss}$, µg/cm$_2$/hr); the intercept of this line on the time axis give the lag time ($t_L$,h).

Examples I–III include skin flux results from various embodiments of a transdermal matrix system according to the present invention containing aconitine-derived alkaloids.

| Formulation | Composition (%, w/w) | $Q_t$ (t = 24) (µg/cm$^2$/t)* |
|---|---|---|
| Adhesive/LAP | 97.5/2.5 | 3.7 ± 2.6 |
| Adhesive/LAP/SMO | 87.5/2.5/10 | 8.2 ± 4.6 |
| Adhesive/LAP/L-DEA | 87.5/2.5/10 | 47.9 ± 18.0 |
| Adhesive/LAP/GMO/LA | 87.5/2.5/10 | 7.9 ± 4.1 |
| Adhesive/LAP/Oleic Acid | 87.5/2.5/10 | 14.9 ± 7.4 |

Adhesive: pressure sensitive acrylic copolymers;
LAP: Lappaconitine;
SMO: Sorbitan Monooleate;
L-DEA: Lauramide DEA;
GMO/LA: Glycerol Monooleate/Lauryl Alcohol
*(Mean ± SD), n = 3 skins, 12 cells.

The above results clearly show that using penetration enhancers significantly increases the skin flux of lappaconitine when compared to a lappaconitine/adhesive matrix as a control.

EXAMPLE II

Examples of other formulations of transdermal matrix systems containing aconitine, or aconitine-derived alkaloids and their derivatives or analogs may be as follows.

| | Composition (%, w/w) |
|---|---|
| Formulation II-1 | |
| Acrylic Adhesives | 50.0–99.5 |
| Aconitine | 0.01–30 |
| Enhancers | 0.01–20 |
| Formulation II-2 | |
| PIB Adhesives | 50.0–99.5 |
| Aconitine | 0.01–30 |
| Enhancers | 0.01–20 |
| Formulation II-3 | |
| Silicone Adhesives | 50.0–99.5 |
| Aconitine | 0.01–30 |
| Enhancers | 0.01–20 |
| Formulation II-4 | |
| Acrylic Adhesive 1 | 1–99.5 |
| Acrylic Adhesive 2 | 1–99.5 |
| Aconitine | 0.01–30 |
| Enhancers | 0.01–20 |
| Formulation II-5 | |
| Acrylic Adhesive | 1–99.5 |
| PIB Adhesive | 1–99.5 |
| Aconitine | 0.01–30 |
| Enhancers | 0.01–20 |
| Formulation II-6 | |
| Acrylic Adhesive | 1–99.5 |
| Silicone Adhesive | 1–99.5 |
| Aconitine | 0.01–30 |
| Enhancers | 0.01–20 |
| Formulation II-7 | |
| Silicone Adhesive | 1–99.5 |
| PIB Adhesive | 1–99.5 |
| Aconitine | 0.01–30 |
| Enhancers | 0.01–20 |
| Formulation II-8 | |
| Eudragit Adhesive* | 50.0–99.5 |
| Aconitine | 0.01–30 |
| Enhancers | 0.01–20 |
| Plasticizers/Tackifiers | 0.01–20 |

*A single Eudragit or mixture of different grades of Eudragits (e.g. NE 30 D, L100, L12/5, S 100, S12/5, L 30 D-55, L100-55, E 100, E12/5, RL 100, RL 12/5, R100, RL PO, RL PM, RL 30 D, RS 100, RS 12/5, RS PM, RS PO,, RS 30 D.)

EXAMPLE III

The gel formulations containing 10 mg/ml lappconitine, 3% Hydroxypropyl methylcellulose and penetration enhancers were also evaluated in accordance with the above-recited protocols.

| Formulation | Composition (%, v/v) | $Q_t$ (t = 24) (µg/cm$^2$/t)* |
|---|---|---|
| EtOH/H2O/Gly | 65/10/25 | 12.0 ± 9.0 |
| EtOH/H2O/Gly/GMO/LA | 65/10/19/3/3 | 71.6 ± 40.8 |
| EtOH/H2O/Gly//L-DEA | 65/10/19/6 | 104.5 ± 64.0 |
| EtOH/H2O/Gly/Oleic Acid | 65/10/19/6 | 23.2 ± 11.8 |

EtOH = Ethanol,
Gly: Glycerin;
GMO: Glyceryl monooleate;
LA: Lauryl alcohol;
L-DEA: Lauramide DEA.
*(Mean ± SD), n = 3 skin3, 12 cells.

The above example clearly shows that penetration enhancers do enhance the flux of lappaconitine from gel type formulations.

EXAMPLE IV

In accordance with the present invention, a hybrid transdermal system may be employed for delivering aconitine and aconitine-derived alkaloids. Such a hybrid system generally contains a polymeric, or other type of reservoir with an adhesive overlay. Bioactive agents may be contained in both the reservoir and the adhesive layer. A wide variety of substances may be used for the reservoir, and include, but are not limited to polymers (including adhesives), solutions, gels, emulsified gels, lotions and creams. Other variations of such a hybrid patch, as well as other particular substances for both the adhesive layer and reservoir will be readily recognized by those skilled in the art. Examples of such hybrid transdermal systems in accordance with the present invention may be as follows.

|  | Composition (%, w/w) |
|---|---|
| Formulation IV-1 |  |
| Matrix |  |
| Acrylic Adhesives | 50–99.5 |
| Aconitine | 0–30 |
| Enhancers | 0–20 |
| Gel |  |
| Ethanol | 0.1–99.5% |
| Propylene Glycol | 0–50% |
| Glycerin | 0–50% |
| Water | 0.1–99.5% |
| Enhancers | 0.01–20% |
| Aconitine | 0.01–30% |
| Gelling agents | 0.01–6% |
| Formulation IV-2 |  |
| Matrix |  |
| PIB Adhesives | 50–99.5 |
| Aconitine | 0–30 |
| Enhancers | 0–20 |
| Gel |  |
| Ethanol | 0.1–99.5% |
| Propylene Glycol | 0–50% |
| Glycerin | 0–50% |
| Water | 0.1–99.5% |
| Enhancers | 0.01–20% |
| Aconitine | 0.01–30% |
| Gelling agents | 0.01–6% |
| Formulation IV-3 |  |
| Matrix |  |
| Silicone Adhesives | 50–99.5 |
| Aconitine | 0–30 |
| Enhancers | 0–20 |
| Gel |  |
| Ethanol | 0.1–99.5% |
| Propylene Glycol | 0–50% |
| Glycerin | 0–50% |
| Water | 0.1–99.5% |
| Enhancers | 0.01–20% |
| Aconitine | 0.01–30% |
| Gelling agents | 0.01–6% |

EXAMPLE V

Aconitine alkaloids can be formulated with other active agents such as analgesics, anti-inflammatories, pain regulators, drugs or agents which impart a sense of well-being, and good health imparting substances, such as herb extracts or other related substances to provide enhanced benefits. The following examples show various aspects of an Aconitine transdermal system having a variety of ingredients as provided by the present invention.

|  | Composition (%, w/w) |
|---|---|
| Formulation V-1 |  |
| Acrylic Adhesive | 50–99.5 |
| Aconitine | 0.01–30 |
| Enhancers | 0.01–20 |
| Melatonin | 0.01–20 |
| Formulation V-2 |  |
| Acrylic Adhesive | 50–99.5 |
| Aconitine | 0.01–30 |
| Enhancers | 0.01–20 |
| Tetrahydropalmatin (Corydalis B) | 0.01–20 |
| Formulation V-3 |  |
| Acrylic Adhesive | 50–99.5 |
| Aconitine | 0.01–30 |
| Enhancers | 0.01–20 |
| Ferulic Acid | 0.01–20 |
| Formulation V-4 |  |
| Acrylic Adhesive | 50–99.5 |
| Aconitine | 0.01–30 |
| Enhancers | 0.01–20 |
| Sinomenine | 0.01–20 |
| Formulation V-5 |  |
| Acrylic Adhesive | 50–99.5 |
| Aconitine | 0.01–30 |
| Enhancers | 0.01–20 |
| Rhynochophylla Alkaloids | 0.01–20 |
| Formulation V-6 |  |
| Acrylic Adhesive | 50–99.5 |
| Aconitine | 0.01–30 |
| Enhancers | 0.01–20 |
| 3-Acetylaconitine | 0.01–20 |
| Formulation V-7 |  |
| Acrylic Adhesive | 50–99.5 |
| Aconitine | 0.01–30 |
| Enhancers | 0.01–20 |
| Anisodin | 0.01–20 |
| Formulation V-8 |  |
| Acrylic Adhesive | 50–99.5 |
| Aconitine | 0.01–30 |
| Enhancers | 0.01–20 |
| Dicentrin | 0.01–20 |
| Formulation V-9 |  |
| Acrylic Adhesive | 50–99.5 |
| Aconitine | 0.01–30 |
| Enhancers | 0.01–20 |
| Anisodamin | 0.01–20 |
| Formulation V-10 |  |
| Acrylic Adhesive | 50–99.5 |
| Aconitine | 0.01–30 |
| Enhancers | 0.01–20 |
| Capsaicin | 0.01–20 |
| Formulation V-11 |  |
| Acrylic Adhesive | 50–99.5 |
| Aconitine | 0.01–30 |
| Enhancers | 0.01–20 |
| Glucosamine | 0.01–20 |
| Formulation V-12 |  |
| Acrylic Adhesive | 50–99.5 |
| Aconitine | 0.01–30 |
| Enhancers | 0.01–20 |
| Vitamin E* | 0.01–20 |

*One or more vitamins can be selected from either water-soluble (e.g. Vitamin B1, B2, B3, B5, B6, B12, B13, B15, B17, Biotin, Choline, Folic acid, Inositol, PABA, Vitamin C, and Vitamin P) or oil soluble vitamins (e.g. Vitamins A, D, E and K).

-continued

| | Composition (%, w/w) |
|---|---|
| Formulation V-13 | |
| Acrylic Adhesive | 50–99.5 |
| Aconitine | 0.01–30 |
| Enhancers | 0.01–20 |
| Amino Acids* | 0.01–20 |

*Amino acids are selected from but not limited to Alanine, Arginine, Carnitine, DLPA, GABA, Glutamate, Glutamine, Glycine, Histidine, Lysine, Methionine, N-Acetyl Cysteine, Ornithine, Phenylalanine, Taurine, Tyrosine, and Valine.

| | |
|---|---|
| Formulation V-14 | |
| Acrylic Adhesive | 50–99.5 |
| Aconitine | 0.01–30 |
| Enhancers | 0.01–20 |
| Minerals* | 0.01–20 |

*One or more minerals necessary to human body can be selected, but not limited to copper, manganese, iron, zinc, calcium, magnesium, chromium, galenium, cobalt, etc.

| | |
|---|---|
| Formulation V-15 | |
| Acrylic Adhesive | 50–99.5 |
| Aconitine | 0.01–30 |
| Enhancers | 0.01–20 |
| Herb/botanical extracts* | 0.01–20 |

*Herb/botanical extracts, which are good for pain relief and drug addiction relief, can be selected from but not limited to, Asarum L. sieboldi Mig., Camphol, Clove (Flos syzygii Aromatici), Corydalis ambigua, Danshen (salvia miltiorrhize), Dongui (Radix angelicae sinensis), Forsythia suspensa (thunb.) Vahl., Ginseng, Ginkgo Biloba, Impatients balsamina L. Ib., Ligusticum wallichii Franch, Myrrha, Olibanum, Pearl, Polygalaceae L., Speranskia tuberculata Bail, St., St. John's Wort, Valerian, etc.

| | |
|---|---|
| Formulation V-16 | |
| Acrylic Adhesive | 50–99.5 |
| Aconitine | 0.01–30 |
| Enhancers | 0.01–20 |
| Anti-oxidant* | 0.01–20 |

*Anti-oxidant agents can be selected from but not limited to Polyphenols, such as Catechins, Beta-carotene, Co-enzyme Q-10, Grapnol, Vitamin C, Vitamin E, etc.

| | |
|---|---|
| Formulation V-17 | |
| Acrylic Adhesive | 50–99.5 |
| Aconitine | 0.01–30 |
| Enhancers | 0.01–20 |
| NSAIDS* | 0.01–20 |

*NSAIDs (Nonsteroidal Antiinflammatory Drugs) are selected from, but not limited to, Butibufen, Carprofen, Celecoxib, Diclofenac, Difluisal, Etodolac, Flurbiprofen, Fennoprofen calcium, Flunixin Meglumine, Ibuprofen, Indomethacin, Ketoprofen, Ketorolac tromethamine, Magnesium Salicylate, Meclofenamate sodium, Mefenamic acid, Naproxen, Nabumetone, Oxaprozin, Phenylbutazone, Piroxicam, Rofecoxib, Sulindac, Tolmetin, and Tiaprofenic acid, etc.

| | |
|---|---|
| Formulation V-18 | |
| Acrylic Adhesive | 50–99.5 |
| Aconitine | 0.01–30 |
| Enhancer | 0.01–20 |
| Narcotic agonist analgesics* | 0.01–20 |

*Narcotic agonist analgesics can be selected from, but not limited to, Alfentanil, Benzylmorphine, Codeine, Desomorphine, Endorphins, Ethylmorphine, Fentanyl, Hydromorphone, Lavorphanol, Levomethadyl Acetate, Meperidine, Methadone, Morphine, Normorphine, Normethadone, Opium, Oxycodone, Oxymorphone, Remifentanil, Sufentanil, and Tilidine, etc.

| | |
|---|---|
| Formulation V-19 | |
| Acrylic Adhesive | 50–99.5 |
| Aconitine | 0.01–30 |
| Enhancers | 0.01–20 |
| Narcotic agonist-antagonist analgesics* | 0.01–20 |

*Narcotic agonist-antagonist analgesics can be selected from, but not limited to, Buprenorphine, Butorphanol, Dezocine, Eptazocine, Methotrimeprazine, Nalbuphine, and Pentazocine, etc.

-continued

| | Composition (%, w/w) |
|---|---|
| Formulation V-20 | |
| Acrylic Adhesive | 50–99.5 |
| Aconitine | 0.01–30 |
| Enhancers | 0.01–20 |
| Anti-migraine Agents* | 0.01–20 |

*Anti-migraine agents can be selected from, but not limited to, seratonin 5-HT receptor agonists, including, but not limited to naratriptan, rizatriptan, sumatriptin, zolmitriptan, salts, derivatives, analogs, prodrugs, and mixtures thereof. Other anti-migraines include, methylsergide maleate and ergotamine derivatives, such as dihydroergotamine mesylate, ergotamine tartrate, etc.

| | |
|---|---|
| Formulation V-21 | |
| Acrylic Adhesive | 50–99.5 |
| Aconitine | 0.01–30 |
| Enhancers | 0.01–20 |
| Antiemetic/antivertigo agent* | 0.01–20 |

*Antiemetic/antivertigo agents include but are not limited to, chloropromazine, perphenazine, prochlorperazine, promethazine, thiethylperazine, triflupromazine, metoclopramide, benzquinamide, cannabinoids, corticosteroids, hydroxyzine HCl, diphenidol, phosphorated carbohydrates, etc.

| | |
|---|---|
| Formulation V-22 | |
| Acrylic Adhesive | 50–99.5 |
| Aconitine | 0.01–30 |
| Enhancers | 0.01–20 |
| Anticholinergics* | 0.01–20 |

*Anticholinergics can be selected from, but not limited to, Adiphenine, Anisotropine, Atropine, Benzetimide, Clidinium,, Deptropine, Dicyclomine, Diponium, Glycopyrrolate, Hydroxyzine, Orphenadrine, Oxybutynin, Propantheline, and Scopolamine, etc.

EXAMPLE VI

The following examples illustrate various topical preparations for aconitine and aconitine-derived alkaloids in accordance with the present invention. Topical formulations, such as, gels, creams, lotions, ointments, paste, mousses, aerosols, etc., may be used to so long as when applied to the desired area of the skin the formulation will stay in place. Further, such formulations may be utilized in connection with an LRS patch.

| | Composition (%, w/w) |
|---|---|
| 1. Gel | |
| Formulation VI-1 | |
| Aconitine | 0.01–40% |
| Ethanol | 0–70% |
| Propylene Glycol | 0–50% |
| Water | 0–95% |
| Glycerin | 0–50% |
| Enhancers | 0–20% |
| Gelling Agents/thickeners | 0.1–6% |
| 2. Cream (o/w) | |
| Formulation VI-2 | |
| Aconitine | 0.01–40% |
| Stearyl Alcohol | 0.1–30% |
| Beeswax | 0.1–20% |
| Sorbitan Monooleate | 0.1–10% |
| Polysorbate 80 | 0.1–10% |
| Methyl Paraben | 0.01–2% |
| Propyl Paraben | 0.01–2% |
| Water | 40–95% |

-continued

| | Composition (%, w/w) |
|---|---|
| 3. Cream (w/o) Formulation VI-3 | |
| Aconitine | 0.01–40% |
| Stearyl Alcohol | 1–30% |
| White Wax | 1–30% |
| Almond Oil | 10–80% |
| Sodium Borate | 0.1–5% |
| Water | 1–50% |
| 4. Vanishing Cream Formulation VI-4 | |
| Aconitine | 0.01–40% |
| Stearic Acid | 0.1–30% |
| Stearyl Alcohol | 0.1–10% |
| Cetyl Alcohol | 0.1–10% |
| Glycerin | 1–30% |
| Methyl Paraben | 0.01–2% |
| Propyl Paraben | 0.01–2% |
| Potassium Hydroxide | 0.01–3% |
| Water | 40–95% |
| 5. Lotion Formulation VI-5 | |
| Aconitine | 0.01–40% |
| White Petrolatum | 0.1–10% |
| Mineral Oil | 0.1–10% |
| Propylene Glycol Stearate | 0.1–10% |
| Stearyl Alcohol | 0.1–10% |
| Benzyl Alcohol | 0.01–5% |
| Propylene Glycol | 0.1–20% |
| Ethanol | 0.1–50% |
| Water | 40–95% |
| 6. Ointment Formulation VI-6 | |
| Aconitine | 0.01–40% |
| White Petrolatum | 50–95% |
| White Wax | 0.1–10% |
| Stearyl Alcohol | 0.1–10% |
| Cholesterol | 0.1–10% |
| 7. Water-washable Ointment Formulation VI-7 | |
| Aconitine | 0.01–40% |
| White Petrolatum | 1–50% |
| Stearyl Alcohol | 1–50% |
| Propylene Glycol | 1–30% |
| Sodium Lauryl Sulfate | 0.01–5% |
| Methyl Paraben | 0.01–2% |
| Propyl Paraben | 0.01–2% |
| Water | 1–40% |

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of ameliorating pain and inflammation in a subject, comprising transdermally administering to said subject, an amount of an aconitine alkaloid selected from the group consisting of: lappaconitine, 3-acetylaconitine, and bulleyaconitine A which is sufficient to achieve an aconitine alkaloid blood plasma level of from about 0.5 to about 400 ng/ml.

2. A method as set forth in claim 1, wherein the transdermal administration the aconitine alkaloid is sufficient to achieve an aconitine alkaloid blood plasma level of from about 0.5 to about 200 ng/ml.

3. A method as set forth in claim 1, wherein the aconitine alkaloid blood plasma level is achieved within about 0.25 to about 18 hours after initiation of the aconitine alkaloid administration.

4. A method as set forth in claim 1, wherein the aconitine alkaloid blood plasma level is achieved within about 0.5 to about 12 hours after initiation of the aconitine alkaloid administration.

5. A method as set forth in claim 1, wherein the aconitine alkaloid blood plasma level is sustained for a duration of at least about 24–96 hours from a single transdermal administration.

* * * * *